(12) United States Patent
Ip et al.

(10) Patent No.: US 6,977,271 B1
(45) Date of Patent: Dec. 20, 2005

(54) METHOD FOR INHIBITION OF ANGIOGENESIS AND VASCULOGENESIS

(75) Inventors: Margot M. Ip, Orchard Park, NY (US); Patricia Masso-Welch, Buffalo, NY (US); Clement Ip, Orchard Park, NY (US); Danilo Zangani, Sassari (IT)

(73) Assignee: Health Research, Inc., Buffalo, NY (US)

( * ) Notice: Subject to any disclaimer, the term of this patent is extended or adjusted under 35 U.S.C. 154(b) by 0 days.

(21) Appl. No.: 10/232,284

(22) Filed: Aug. 30, 2002

Related U.S. Application Data (60) Provisional application No. 60/316,131, filed on Aug. 30, 2001.

(51) Int. Cl.$^7$ ............................................. A61K 31/20
(52) U.S. Cl. ...................................................... 514/560
(58) Field of Search ........................................ 514/560

(56) References Cited

U.S. PATENT DOCUMENTS

| | | | |
|---|---|---|---|
| 5,827,885 A * | 10/1998 | Cook et al. .................. | 514/558 |
| 6,242,621 B1 * | 6/2001 | Jerome et al. ............... | 554/224 |
| 6,426,367 B1 * | 7/2002 | Das ............................. | 514/560 |
| 2002/0010211 A1 * | 1/2002 | Obukowicz et al. ........ | 514/549 |
| 2002/0077317 A1 * | 6/2002 | Das ............................. | 514/171 |

OTHER PUBLICATIONS

Ip et al, Cancer Epidemiol.Biomarkers Prev., vol. 9(7), pp. 689-696 (abstract) Jul. 2000.*
Kim et al, Derwent KR2001103471, Nov. 2001.*
Ip, Oncology News, vol. 9(11), Nov. 2000.*
Aro, et al., *Inverse Association Between Dietary and Serum Conjugated Linoleic Acid and Risk of Breast Cancer in Postmenopausal Women*, Nutrition and Cancer, 2000, 38(2), pp. 151-157.
Bougnoux, et al., *Polyunsaturated Fatty Acids and Breast Cancer*, LIpids, 1999, vol. 34, p. S99.
Belury, et al., *Dietary Conjugated Linoleic Acid Modulation of Phorbol Ester Skin Tumor Promotion*, Nutrition and Cancer, 1996, vol. 26, No. 2, pp. 149-157.
Cesano, et al., *Opposite Effects of Linoleic Acid and Conjugated Linoleic Acid on Human Prostatic Cancer in SCID Mice*, Anticancer Research, 1998, 18, 833-838, pp. 1429-1434.
Ha, et al., *Inhibition of Benzo(a)pyrene-Induced Mouse Forestomach Neoplasia by Conjugated Dienoic Derivatives of Linoleic Acid*, Cancer Research, Feb. 15, 1990, 50, pp. 1097-1101.
Hubbard, et al., *Reduction of Murine Mammary Tumor Metastisis by Conjugated Linoleic Acid*, Cancer Letters, 2000, 150, pp. 93-100.
Igarashi, et al., *Newly Recognized Cytotoxic Effect of Conjugated Trienoic Fatty Acids on Cultered Human Tumor Cells*, Cancer Letters, 2000. 148, pp. 173-179.

Ip, et al., *Conjugated Linoleic Acid: A Powerful Anticarcinogen from Animal Fat Sources*, Cancer Prevention, Aug. 1, 1994, vol. 74, No. 3, pp. 1050-1054.
Ip, et al., *Conjugated Linoleic Acid Isomers and Mammary Cancer Prevention*, Nutrition and Cancer, 2002, 43(1), pp. 52-58.
Ip, et al., *Conjugated Linoleic Acid Suppresses Mammary Carcinogensis and Proliferative Activity of the Mammary Gland in the Rat*, Cancer Research, Mar. 1, 1994, 54, pp. 1212-1215.
Ip, et al., *The Efficacy of Conjugated Linoleic Acid in Mammary Cancer Prevention in Independent of the Level or Type of Fat in the Diet*, Carcinogenesis, 1996, vol. 17, No. 5, pp. 1045-1050.
Ip, et al., *Mammary Cancer Prevention by Conjugated Dienoic Derivative of Linoleic Acid*, Cancer Research, Nov. 15, 1991, 51, pp. 6118-6124.
Ip, et al., *Retention of Conjugated Linoleic Acid in the Mammary Gland is Associated with Tumor Inhibition During the Post-Initiation Phase of Carcinogenesis*, Carcinogenesis, 1997, vol. 18, No. 4, pp. 755-759.
Ip, (Margot) et al., *Conjugated Linoleic Acid Inhibits Proliferation and Induced Apoptisis of Normal Rat Mammary Epithelial Cells in Primary Culture*, Experimental Cell research, 1999, 250, pp. 22-34.
Ip, (Margot) et al., *Conjugated Linoleic Acid Acts Directly on the Mammary Epithelium and Indirectly Through the Mammary Stroma to Prevent Breast Cancer*, J. Nutr., 2001, 131, p. 189S.
Knekt, et al., *Intake of Dairy Products and the Risk of Breast Cancer*Br. J. Cancer, Mar. 1996, 73(5), pp. 687-691.
Liew; et al., *Protection of Conjugated Linoleic Acids Against 2-Amino-3-Methylimidazo [4,5-f] Quinoline-Induced Colon Carcinogenesis in the F344 Rat: A Study of Inhibitory Mechanisms*, Carcinogenesis, 1995, vol. 16., No. 12, pp. 3037-3043.
Masso-Welch, et al., *Inhibition of Angiogenesis by the Cancer Chemopreventive Agent Conjugated Linoleic Acid*, Cancer Research, Aug. 1, 2002, 62, pp. 4383-4389.
Thompson, et al., *Morphological and Biochemical Status of the Mammary Gland as Influenced by Conjugated Linoleic Acid: Implication for a Reduction in Mammary Cancer Risk*, Cancer Research, Nov. 15, 1997, 57, pp. 5067-5072.
Visonneu, et al., *Conjugated Linoleic Acid Suppresses the Growth of Human Breast Adenocarcinoma Cells in SCID Mice*, Anticancer Research, 1997, 17, pp. 969-974.
Ip et al., *Conjugated Linoleic Acid Acts Directly on the Mammary Epithelium and Indirectly Through the Mammary Stroma to Prevent Breast Cancer*, J. Amer. Coll. Nutr., Oct. 200, vol. 19, p. 677.

* cited by examiner

*Primary Examiner*—Christopher S. F. Low
*Assistant Examiner*—C. Delacroix-Muirheid
(74) *Attorney, Agent, or Firm*—Hodgson Russ LLP (57) ABSTRACT

The present invention provides a method for inhibiting or preventing angiogenesis in animals and humans comprising the steps of administering to the animal or human an effective amount of one or more isomers of conjugated linoleic acid ("CLA"). The CLA may be administered in the form of a free fatty acid, an ester, or as a salt, in a pill, or as a component of a natural or prepared food product.

9 Claims, 8 Drawing Sheets

Figure 8

METHOD FOR INHIBITION OF ANGIOGENESIS AND VASCULOGENESIS

This application claims priority of U.S. Provisional application No. 60/316,131, filed on Aug. 30, 2001, the disclosure of which is incorporated herein by reference.

"This invention was made with Government support under grant no. CA61763 awarded by the National Institutes of Health and grant no. DAMD17-00-1-0286 awarded by the U.S. Department of Defense. The Government has certain rights in the invention."

FIELD OF THE INVENTION

This invention relates generally to the field of angiogenesis and more particularly provides a method for the inhibition of angiogenesis and vasculogenesis in humans and animals.

BACKGROUND OF THE INVENTION

In order for cancer cells to multiply and grow into a tumor, they must develop a blood supply to furnish the cells with needed nutrients and oxygen. This process of the development of new blood vessels is termed angiogenesis and/or vasculogenesis, and has been the subject of intense investigation by scientists and drug companies, whose focus has been on understanding the mechanism by which blood vessel formation is initiated, as well as finding drugs which inhibit this process. It is hypothesized that a drug which blocks blood vessel formation will inhibit the growth of tumors, or their metastases, by cutting off the necessary supply lines which feed the tumor.

A limitation of current anti-angiogenic therapy is the necessity for providing continuous levels of a potentially expensive and/or toxic agent on a long-term basis. In contrast, the ability to provide an inexpensive, non-toxic and effective agent in food or in pill form would circumvent this limitation. Thus, there is an ongoing need for identification of new anti-angiogenic agents that can be used for therapeutic and preventive purposes.

BRIEF DESCRIPTION OF THE DRAWINGS

FIG. 1 is a photomicrographic representation showing that dietary CLA inhibits cellular recruitment and the formation of functional blood vessels in response to Engelbreth-Holm-Swarm sarcoma—derived reconstituted basement membrane (EHS-RBM) angiogenic challenge. Subcutaneous EHS-RBM injection in mice fed the control (A–D) or 1% CLA (E–H) diets results in the formation of a fibrocellular capsule (arrows), from which cellular invasion (arrowhead) originates. A and B show the dense cellular infiltrate in mice fed the control diet. The cellular network in mice fed the 1% CLA diet (E,F) is considerably less dense. The cellular network in mice fed the control diet (C,D) is composed of interconnecting solid cords of cells (white arrowheads) or tubules with patent lumen containing red blood cells (black arrowheads, longitudinal view, arrows show a transverse view; panel D shows a higher magnification view of the same field in C). In contrast, the cellular network in mice fed a diet with 1% CLA is largely composed of solid cellular cords (white arrowheads), most of which have no lumen and no red blood cells within (G,H). Magnification bars in panels A and E represent 500 $\mu$m, and 250 $\mu$m in panels B and F. Magnification bars in panels C, D, G and H represent 50 $\mu$m. P, ECM pellet; MG, mammary gland.

SUMMARY OF THE INVENTION

The present invention provides a method for inhibition of angiogenesis in an individual diagnosed with a solid tumor. The method comprises administering orally a therapeutically effective dose of one or more isomers of conjugated linoleic acid (CLA) such that angiogenesis in the tumor is reduced following administration of the CLA isomer or isomers.

The present invention also provides a method for prevention of the occurrence or severity of solid tumors comprising identifying individuals with a high risk of developing solid tumors (such as breast cancer) and administering one or more isomers of CLA.

DESCRIPTION OF THE INVENTION

The present invention provides a method for inhibiting the development of blood vessels in animals and humans. The method comprises the steps of administering a therapeutically effective or prophylactically effective amount of Conjugated Linoleic Acid (CLA) to the individual in need of treatment.

Individuals in need of treatment include those who have been diagnosed with cancer, in particular with a solid tumor. Also included are individuals who are at a high risk of developing cancer. The risk factors for developing cancer are well known to those skilled in the art. For example, the risk of developing breast cancer in women increases with age, with lower age of menarche (as an example, age of first menstruation age 11 or younger), with increased age at first birth, with increasing number of first degree relatives with breast cancer (sister, mother), in women who have had previous breast biopsies, in women who have had at least one biopsy with atypical hyperplasia, in women who have already had breast cancer; etc.

Conjugated linoleic acid is a term used herein as meaning any of a collection of positional and geometric isomers of octadecadienoic acid (a fatty acid with 18 carbon atoms) with conjugated double bonds. Some of the isomers are found naturally in dairy products, including milk and cheese, as well as the meat of ruminants; others can be readily synthesized. CLA isomers that have been identified in food include, but are not limited to: cis-9, trans-11 CLA (the major isomer), as well as isomers of octadecadienoic acid with conjugated double bonds located in either the cis or trans configuration at positions $\Delta 7,9$-, $\Delta 8,10$-, $\Delta 9,11$-, $\Delta 10,12$-, $\Delta 12,14$ and $\Delta 11,13$- of the carbon chain (Chin et al, 1992; Lavillonniere et al, 1998; Yurawecz et al, 1998; Parodi, 1997; Sehat et al, 1998). Methods for the synthesis of CLAs have also been described in U.S. Pat. Nos. 5,986,116 and 6,242,621.

CLA has been shown to inhibit two stage dimethylbenz (a)anthracene (DMBA)-induced mouse epidermal carcinogenesis (Ha et al, 1987; Belury et al, 1996), benzo(a)pyrene (BP)-induced mouse forestomach neoplasia (Ha et al, 1990), DMBA- and N-nitroso-N-methylurea (NMU)—induced rat mammary carcinogenesis (Ip et al, 1991; Ip et al, 1994; Ip et al, 1995), and the incidence of 2-amino-3-methylimidazo[4,5-f]quinoline-induced aberrant crypt foci in the rat colon (Liew et al, 1995). Moreover, CLA was found to reduce both the size and metastatic spread of human MDA-MB468 breast cancer cells and DU-145 prostatic tumor cells in SCID mice (Visonneau et al, 1997; Cesano et al, 1998).

The advantage of using CLA is that it is effective at low levels in the diet. Moreover, the feasibility of increasing the CLA content of foods has already been demonstrated (Stanton et al 1997; Kelly et al, 1998; Garcia et al, 1998), suggesting the practicality of this normal food component in long-term cancer prevention. The preferred mode of administration of CLA is oral. Natural or synthetic CLA may also be provided to humans in pill form, or as a component of a natural or prepared food product. U.S. Pat. No. 6,242,621 describes several formulations for consumption of CLA (incorporated herein by reference). CLA may be formulated with suitable carriers such as starch, sucrose or lactose in tablets, capsules, solutions and emulsions. Various doses for human and animal consumption are disclosed in U.S. Pat. No. 6,242,621.

Any CLA isomer or a CLA isomer blend comprising one or more isomers can be used in the present invention. The composition can include isomers as the free conjugated linoleic acid, or as a non toxic salt (for example a sodium, potassium or calcium salt), or in the form of a triglyceride or other non toxic esters. It can be administered in the form of a natural or prepared food product, or in pill form. The exact amount of CLA to be administered will depend upon the weight of the individual. The amount generally ranges from about 0.001 g/kg to about 2.5 g/kg. CLA is non toxic, and has not been reported to damage existing blood vessels.

In one embodiment of the invention, the CLA isomers or a CLA isomer blend is fed to individuals who have been diagnosed with cancer. This can be done in combination with other therapeutic regimens such as chemotherapy, radiotherapy or surgical removal of the tumor. This invention is particularly suited for therapy of solid tumor. In one embodiment, CLA is administered orally to individuals diagnosed with breast cancer. The effect of CLA on angiogenesis in tumors can be monitored by standard procedures to evaluate tumor size etc by techniques which are known in the art. In another embodiment, CLA may be administered on a long-term basis to individuals who are at a high risk of developing cancer.

The following examples are provided for illustrative purposes and are not intended to be restrictive.

EXAMPLE 1

Materials and Methods

CLA from Nu-Chek Prep Inc. (Elysian, Minn.), containing 85–88% c9,t11 and t10,c12 CLA at an approximate 1:1 ratio, as well as trace amounts of other isomers, was used in the in vivo studies, as wells as the in vitro studies where noted. For in vitro studies, highly purified (>95%) CLA isomers from Natural ASA (Hovdebyda, Norway) were used. Heparan sulfate, 3,3',5,5'-tetramethyl benzidine liquid ELISA substrate, and PMSF were purchased from Sigma (St. Louis, Mo.). Basic FGF was obtained from Biodesign (Kennebunk, Me.). The VEGF ELISA kit was purchased from R&D Systems (Minneapolis, Minn.). Rabbit antisera against VEGF-A (SC-7269) and Flk-1 (SC-505) were purchased from Santa Cruz Biotechnology (Santa Cruz, Calif.). Mouse anti-hsc70 antibody (SPA-820) was obtained from Stressgen (Victoria, BC, Canada). Leupeptin was purchased from Boehringer-Mannheim (Indianapolis, Ind.), and soybean trypsin inhibitor from Calbiochem (La Jolla, Calif.). ECL (detection substrate used for hsc70 western blots) and ECL-plus (detection substrate used for Flk-1 and VEGF western blots) were obtained from Amersham (Arlington Heights, Ill.). Donkey anti-rabbit and anti-mouse secondary antibodies conjugated to HRP were purchased from Jackson Immunoresearch Laboratories (Westgrove, Pa.). Trans-blot (pure nitrocellulose) Transfer Membrane was purchased from Bio-Rad (Hercules, Calif.). Reconstituted basement membrane was extracted from the EHS mouse sarcoma as previously described (Darcy et al., 2000).

Animal Care

CD2/F1 mice were purchased from the NCI Frederick Cancer Research Facility, Biological Testing Branch (Frederick, Md.), and were given water ad libitum. Animals were fed semi-synthetic AIN-76A diets containing 5% (w/w) corn oil, without or with supplementation with 1% or 2% CLA as described previously (Ip et al., 1994). CD2/F1 mice, fed a chow diet, were also used to carry the EHS sarcoma (Darcy et al., supra). This tumor has been passaged in CD2/F1 mice in our lab for the past fifteen years. Animal rooms were air-conditioned and humidity-controlled, with a light cycle of 12 hours on and 12 hours off. Animals were housed in accordance with the standards set by the NIH and the Roswell Park Cancer Institute Animal Care and Use Committee.

In vivo EHS-RBM Angiogenesis Assay

To determine the effects of dietary CLA on angiogenesis, the in vivo angiogenesis model of Kibbey et al., 1992 was utilized. Briefly, CD2/F1 female mice were placed on diets with or without CLA at 8 or 12 weeks of age, with 10–12 mice per group per experiment. After 6 weeks of diet, mice were given bilateral injections of EHS-RBM containing 1.25 µg/ml bFGF and 60 µg/ml heparan sulfate using a 25-gauge needle, into the region of mammary gland four. Mice were sacrificed 7 days after injection. Blood was collected from the trunk for preparation of plasma for analysis of VEGF levels. Pellets and adjacent normal mammary gland tissue were removed and formalin fixed for paraffin embedding. This experiment was repeated four times.

Alternately, for analysis of whole mammary gland levels of VEGF and Flk-1, 10 mice per group were placed on diet at 8 weeks of age, and mice were sacrificed 7 weeks after diet initiation. Mammary glands were snap-frozen in liquid nitrogen to be utilized for preparation of whole gland lysates.

Analysis of Cellular Invasion

Microsope visual fields, visualized with a 20× objective were analyzed for cellular invasion, and with a 40× objective for the presence of functional blood vessels, for a final magnification of 200 or 400×, respectively. The ability of dietary CLA to affect cellular invasion into the EHS-RBM pellet was analyzed on H&E-stained paraffin sections by counting the number of nuclei per field, excluding all acellular regions that remained uninvaded. A total of 68 fields were assessed in 13 pellets from mice on control diets, 75 fields were assessed from 9 pellets from mice on 1% CLA diets, and 62 fields analyzed from 13 pellets, obtained from mice on 2% CLA diets. We analyzed all pellets retrieved from the animals; there was a decline in the number of visible pellets in CLA-fed animals.

Analysis of Functional Blood Vessel Formation

Functional angiogenesis was quantified by determining the number of cell-lined structures with patent lumen and red blood cells. H&E stained paraffin sections were visualized by epifluorescent illumination; red blood cells are strongly fluorescent due to their intensely eosinophilic cytoplasm. This intensity is easily distinguished from the dimly fluorescent nucleated cells. The relative dimness of nucleated cells may be partly due to the presence of nuclear and/or cytoplasmic hematoxylin, which quenches fluorescence. A total of 162 fields were analyzed from 21 slides from control diet animals, 158 fields were analyzed from 21 slides from 1% CLA diet animals, and 174 fields were analyzed from 13 slides from 2% CLA diet animals.

Serum VEGF Analysis

Serum VEGF (VEGF-A) levels were assessed by ELISA using a commercial kit (Quantikine M mouse VEGF ELISA, R&D Systems), as per the manufacturer's instructions. VEGF levels were assessed in sera from mice which had been on diet for a total of 7 weeks, and had received EHS-RBM angiogenic challenge 1 week prior to sacrifice. These data represent the results of four individual experiments, with ten or more animals per diet per trial.

Analysis of VEGF and Flk-1 Expression in Mammary Gland Lysates

Whole mammary glands (gland four) were dissected after sacrifice from mice fed control- or CLA-supplemented diets, snap-frozen in liquid nitrogen and stored at $-80°$ C. Lysates were prepared by pulverizing the frozen glands in a liquid nitrogen-cooled metal pulverizer to a fine powder. The powder was weighed in a pre-tared microfuge tube, and resuspended in ice-cold Triton X-100 lysis buffer (50 mM Tris, pH7.5 at room temperature, 250 mM NaCl, 5 mM EDTA, 0.1% (v/v) Triton X-100, supplemented with 0.1 mM PMSF, 20 ng/ml leupeptin and 100 ng/ml soybean trypsin inhibitor) using 2 ml per gram of tissue. The powder was then homogenized in an ice-cold microfuge tube, using 10–15 strokes of a fitted glass homogenizer. Samples were incubated on ice for 30 minutes, and then centrifuged for 10 min at $4°$ C. at 8,000×g. The supernatants were then aliquoted and frozen at $-20°$ C. An aliquot of the sample was used to determine protein concentration, using the Bio-Rad protein assay. Immediately before electrophoresis, samples were prepared for loading by adding 4× Laemmli SDS-sample buffer at a 1:3 ratio to the thawed sample. The sample was then boiled, sonicated, and centrifuged for 10 min at $4°$ C., 8,000×g in a microfuge, before loading supernatant. Lysates from 7 mice per dietary group were analyzed.

Lysates were loaded using equal protein per well, and proteins were separated on a 7.5% reducing SDS-gel according to the method of Laemmli well known in the art. Proteins were transferred to nitrocellulose using a Bio-Rad Transblot Apparatus (Hercules, Calif.). Blots were blocked with Blotto (TBS (10 mM Tris, pH 8.0, 150 mM NaCl), 0.5% Tween 20, 5% (w/v) non-fat dry milk). All antibody incubations and subsequent rinses were performed in Blotto, with vigorous rocking. Rabbit anti-VEGF-A was used at a final concentration of 2 µg/ml, and rabbit anti-Flk-1 was used at a final concentration of 1 µg/ml. To control for variability in loading, the same blots used for VEGF were stripped and probed for Flk-1. The blots were then stripped again and probed with mouse antisera to hsc70, at a 1:20,000 final concentration. Hsc70 was used as a control for cellular protein loading of western blots, as a constitutively expressed cytoplasmic housekeeping protein. Because dietary CLA causes substantial changes in the cellular and extracellular composition of the mouse mammary gland (Masso-Welch et al., manuscript in preparation), total protein loading by BioRad assay is not descriptive of the cellularity of the whole gland lysate. After binding and washing 5×5 min in Blotto, secondary HRP-conjugated donkey anti-rabbit or donkey anti-mouse antibodies were added at 1:5,000 in Blotto. Blots were washed 5×5 min in Blotto, then 3×3 min with TBS prior to detection of HRP-conjugated secondary antibody using ECL (hsc70) or ECL-plus (VEGF and Flk-1) and exposure of Kodak X-Omat X-ray film. Specific antibody-reactive bands were quantified by densitometry using a Model 300A Scanning Laser Densitometer and ImageQuant software (Molecular Dynamics).

Effects of CLA on Tubule Formation in vitro

An in vitro angiogenesis assay, the formation of microcapillary networks by rat mammary stromal vascular precursor cells on the angiogenic substrate, EHS-RBM, was used to compare the isomer- and concentration-dependent effects of mixed CLA isomers and c9,t11- and t10,c12-CLA. Rat mammary stromal cells (MSC) have the ability to act as true vascular precursors and were isolated from mammary glands as described (Zangani et al., 1999).

CLA-containing media was prepared as follows. Briefly, 18.1 μl of 5N NaOH was added to 28.2 μl of CLA (0.9 g/ml, FW 280) in a small Erlenmeyer flask, followed by vortexing, to make the sodium salt. Warm fetal calf serum (10 ml) was added, sonicated 3–4× with brief pulses (5 sec each), and then gassed with nitrogen and the flask sealed with parafilm. The mixture was incubated in a sonicating water bath for 30 min, followed by 5 min incubation in a 50° C. water bath. FBS (11.9 ml) was added to the flask, to bring the CLA to a final 33× concentration (4.125 mM). This 33×CLA stock solution was added to F12/DME stock and filtered through a 0.22 μM filter to make a sterile 125 μM stock, which was then used to prepare the other media concentrations, such that all CLA media had a final total concentration of 3% FBS.

Early passage MSC (prior to passage 4) were cultured in a 24 well plate at $2 \times 10^4$ cells/well, plated onto 0.4 ml EHS-RBM in the presence of phenol red free F12/DME with 3% FCS, supplemented with 0, 25, 50, 75, 100 or 125 μM CLA. After 7 days in culture, when the cells had formed multiple colonies of three-dimensional networks of tubules (Zangani et al., 1999), capillary networks were photographed, and the extent of network formation was assessed by measuring four planar diameters, at 45° intervals, of the branching colonies. The five largest colonies in each of three wells per group were assessed, for a total of fifteen colonies for each concentration of CLA per experiment. This experiment was replicated twice.

Statistics

Data were analyzed using SigmaStat 2.0 (Jandel Scientific). Analysis of serum VEGF and pellet invasion, cellularity and blood vessel formation, and in vitro capillary network formation were analyzed by performing ANOVA for parametric data (serum VEGF levels) and Kruskall-Wallis ANOVA on Ranks for nonparametric data (cell invasion, cellularity and functional angiogenesis of EHS-RBM pellet). For western blot analysis of whole mammary gland lysates, Tukey Multiple Comparisons was done for parametric data; Dunn's Multiple Comparisons, and/or All Pairwise Multiple Comparison Procedures (Dunnett's Method) were performed for nonparametric data. $P<0.05$ was considered statistically significant. Data are presented as mean SEM.

Results

The mammary glands of humans and animals have many cell types. Cancers usually develop in the epithelium. However the epithelium is surrounded by stroma which can significantly affect the growth of both normal and cancerous epithelium. Stromal cells include fat cells, connective tissue cells, and blood vessels. Previously, the inventors isolated stromal stem cells from rat and mouse mammary glands and found that in tissue culture they could be induced to form capillary-like blood vessels, fat cells, or fibroblasts, depending on the culture conditions (Zangani et al, 1999). The method of isolation of stromal cells is described in Zangani et al., 1999, incorporated herein by reference. The formation of capillary-like blood vessels requires that the mammary stromal stem cells be grown on a gel derived from extracellular matrix proteins, herein termed ECM gel or EHS-RBM gel. The preparation of ECM gel is described in Darcy et al. (2000), incorporated herein by reference. Alternatively, the mammary stromal cells can be grown on substrates such as Matrigel®.

In the present invention, it was unexpectedly observed that CLA inhibited the formation of capillaries and reduced VEGF and VEGF receptor levels.

CLA Inhibits the Formation of Functional Blood Vessels in Vivo

Figure 1:
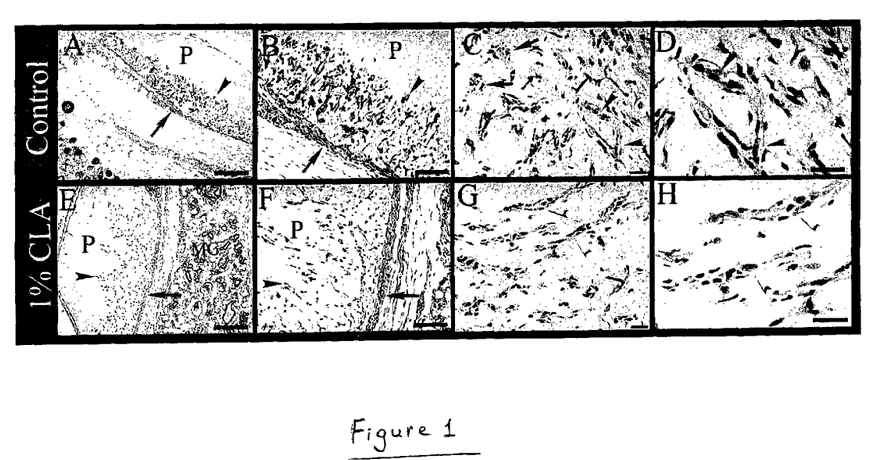

Subcutaneous injection of EHS-RBM supplemented with bFGF and heparan sulfate results in the formation of interconnecting networks of cells within the pellet, 1 week after injection (FIG. 1, arrowheads). A fibrocellular capsule containing multiple cell types (predominantly fibroblasts and polymorphonuclear cells), extracellular matrix and blood vessels forms around the pellet (FIGS. 1A,B,E,F, arrows). At higher magnification, it can be seen that the cellular network in mice fed the control diet is composed of interconnecting tubules with patent lumen containing red blood cells (FIGS. 1C,D, arrowheads). In contrast, the cellular network in mice fed a diet with 1% or 2% CLA is largely composed of flattened, solid cords of cells, most of which have collapsed lumen and no red blood cells within (FIGS. 1G,H, white arrowheads).

Figure 2:
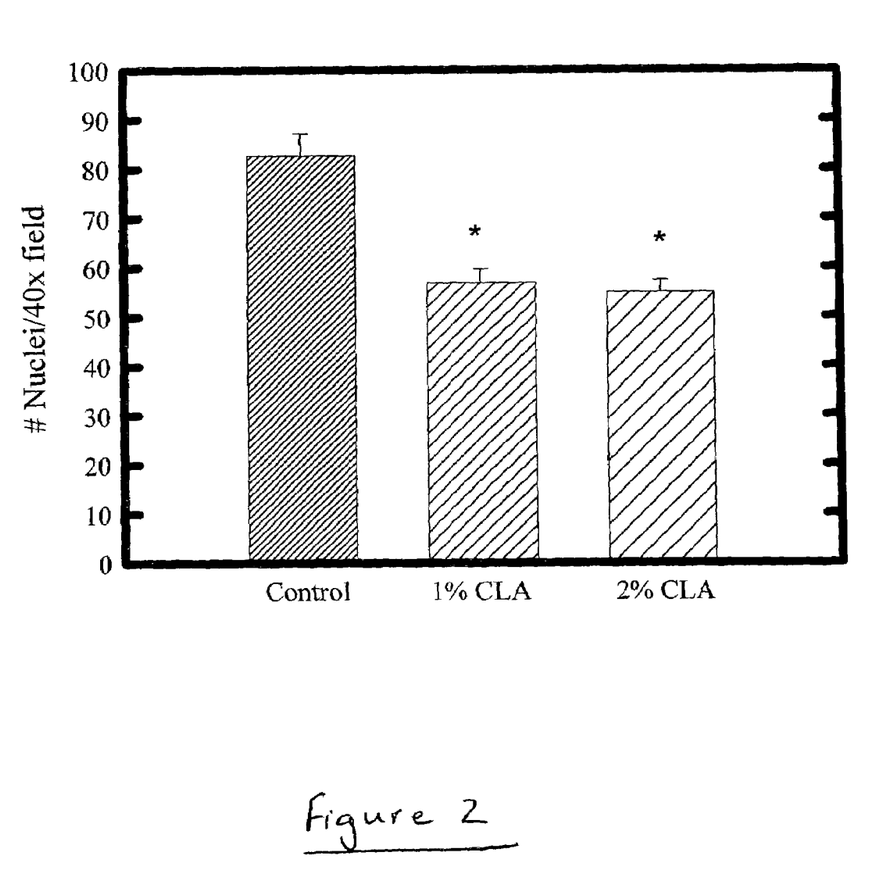
FIG. 2 is a representation of the number of nuclei per field of the EHS-RBM pellet for: controls, animals fed 1% CLA or animals fed 2% CLA demonstrating that CLA inhibits the invasion of blood vessel-forming cells into the pellet.

FIG. 2 shows the results of quantitative analysis of these pellets. The pellets of CLA-fed mice showed a significantly decreased cellular invasion, quantified as the number of nuclei per field in the invaded regions, compared to the pellets of mice fed control diets (FIG. 2). Despite the decrease in total cellularity, the average measured depth of cellular infiltration of the pellet was not different in the control and CLA-fed mice (data not shown).

Figure 3:
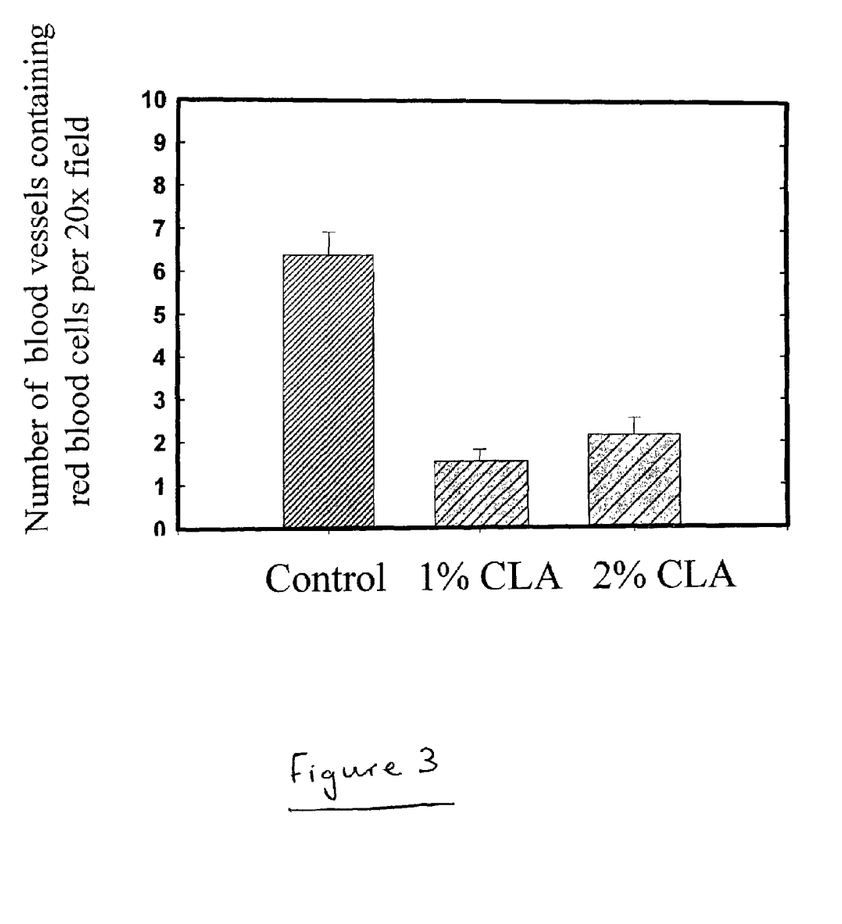
FIG. 3 is a representation of the number of blood vessels containing red blood cells in the EHS-RBM pellet for: controls, animals fed 1% CLA or animals fed 2% CLA demonstrating that CLA inhibits the formation of functional blood vessels.

The abundance of functional capillaries (cellular structures containing red blood cells) was quantified to determine the effects of dietary CLA on functional angiogenesis (i.e. the development of blood-conducting tubules). FIG. 3 demonstrates that both the 1% CLA and 2% CLA diets significantly decreased functional angiogenesis within the EHS pellet, compared to mice fed the control diet. There was no significant difference between 1% and 2% CLA.

Figure 4:
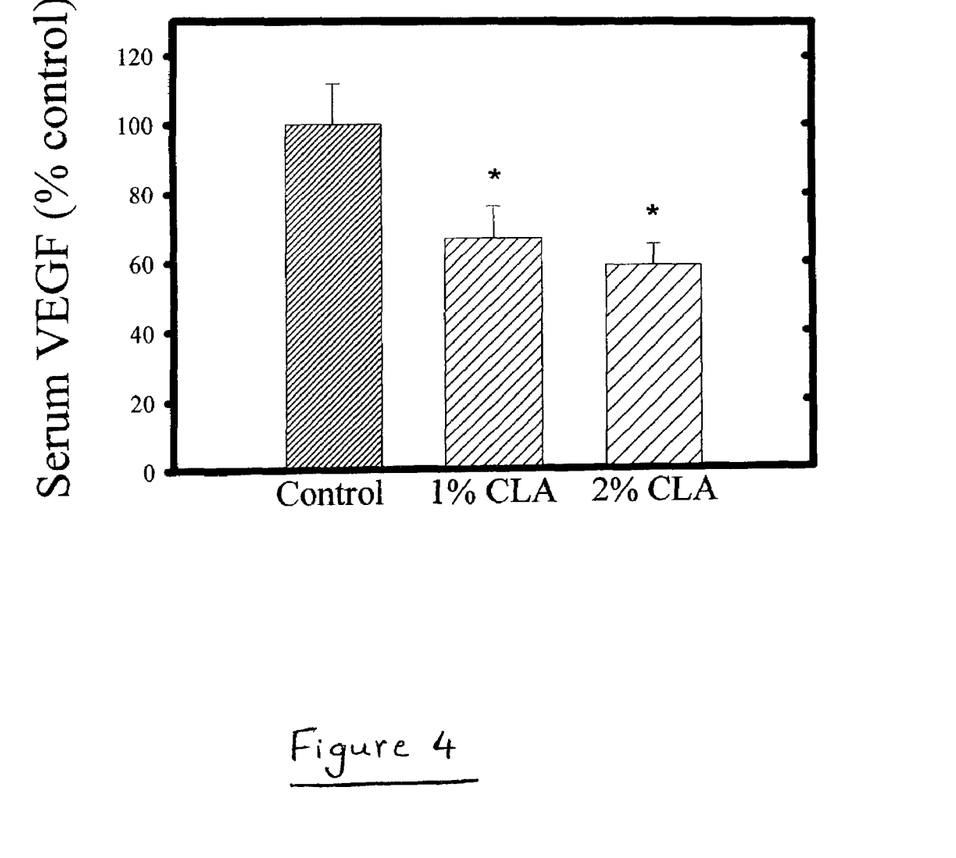
FIG. 4 is a representation of the serum (vascular endothelial growth factor) (VEGF) levels after injection with EHS-RBM pellet for: controls, animas fed 1% CLA and animals fed 2% CLA demonstrating that dietary CLA decreases serum VEGF levels.

Dietary CLA Decreases VEGF Serum Levels and VEGF and Flk-1 Protein in the Mammary Gland In order to determine how CLA might mediate its inhibitory effects on angiogenesis, serum VEGF-A (referred to hereafter as VEGF) concentrations were analyzed 7 days after angiogenic challenge (injection with EHS-RBM). FIG. 4 demonstrates that feeding with both the 1% CLA and 2% CLA diets for 7 weeks significantly reduced average serum VEGF levels by approximately 40%, relative to control diet.

Figure 5A:
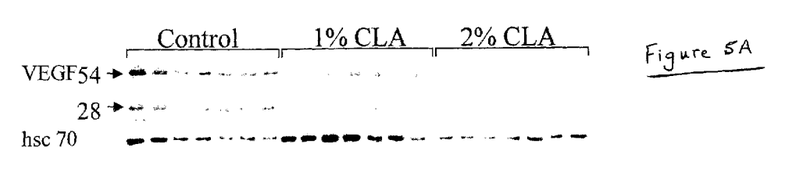
FIG. 5A is a western blot of mammary gland lysates from individual mice fed control or CLA-containing diets showing bands for VEGF (54 and 28 kDa in size) demonstrating that dietary CLA decreases levels of vascular endothelial growth factor (VEGF) in the mammary gland. hsc 70 staining is used as a loading control.
Figure 5B:
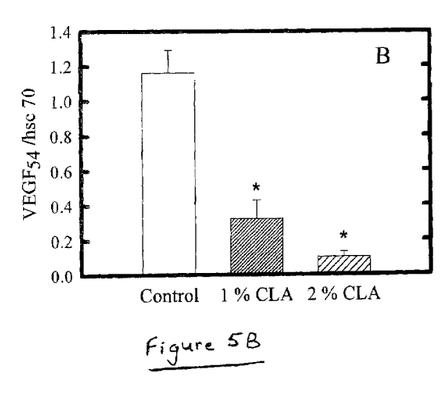
FIGS. 5B and 5C are representations of scanning densitometer results of the VEGF54 or VEGF28 bands from FIG. 5A standardized to the amount of hsc 70. These figures provide quantitative data to indicate that mammary gland levels of VEGF54 and VEGF28 are decreased in mice fed CLA-containing diets.
Figure 5C:
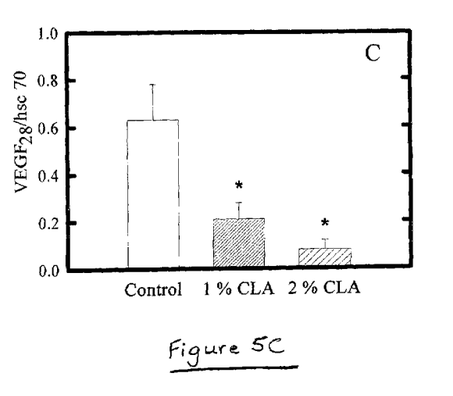

This systemic effect of CLA on serum VEGF was only significant in mice stimulated by angiogenic challenge (pellet injection), which substantially increased baseline levels of VEGF (data not shown). If the effect of CLA were to be physiologically relevant however, we would expect to see a local effect of dietary CLA on mammary gland VEGF, in the absence of angiogenic challenge. To examine this, mice were fed diets with or without CLA for 7 weeks, and whole mammary gland lysates were analyzed by western blotting for VEGF. VEGF protein, detected as 28 and 54 kDa reactive bands in these tissue lysates, was dramatically downregulated in the mammary glands obtained from mice fed CLA (FIG. 5A). These results were quantified by scanning densitometry, and both bands were normalized to hsc70 levels, to compensate for changes in cellularity of mammary glands from CLA-fed mice. As shown in FIG. 5B, both VEGF antibody-reactive bands were significantly decreased by dietary CLA in a dose-dependent manner.

Figure 6A:
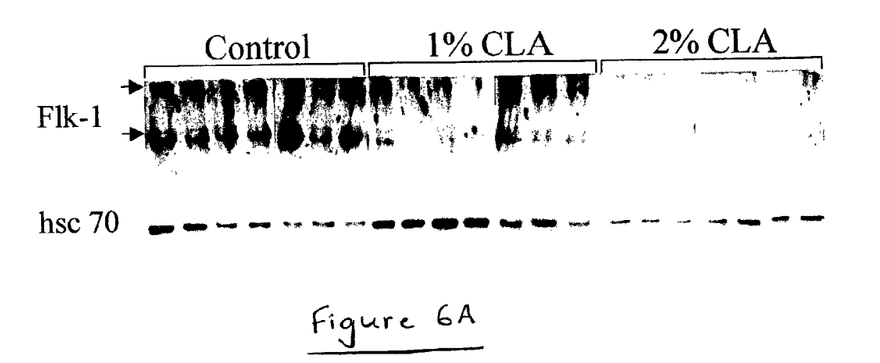
FIG. 6A is a western blot of mammary gland lysates from individual mice fed: control or CLA-containing diets showing that dietary CLA decreases levels of VEGF receptor flk-1 in the mammary gland. hsc 70 staining is used as a loading control.
Figure 6B:
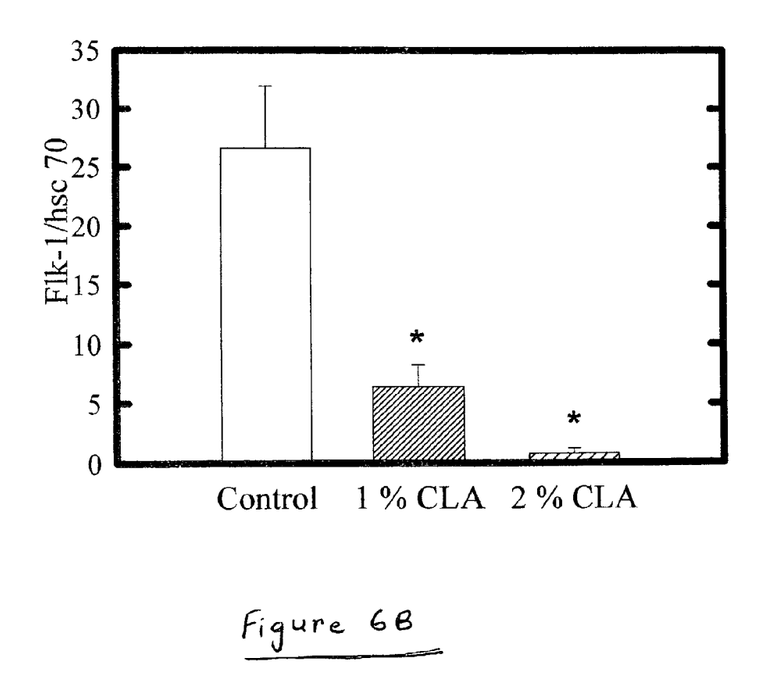
FIG. 6B is a representation of scanning densitometer results of the flk-1 band from FIG. 6A standardized to the amount of hsc 70 for: control, animals fed 1% CLA or animals fed 2% CLA. This figure provides quantitative data to indicate that mammary gland levels of the VEGF receptor flk-1 are decreased in mice fed CLA-containing diets.

Western blotting for Flk-1 was also performed to examine whether there was a coordinate down-regulation of VEGF receptor 2. As shown in FIG. 6A, Flk-1 protein was downregulated by dietary CLA. Control diet-fed animals showed consistently high levels of both a 200 kDa Flk-1 antibody-reactive band, as well as a lower molecular weight (60 kDa) form. Both endothelial cells and 3T3 fibroblasts have been shown to express multiple processed forms of Flk-1 protein (Takahashi et al., 1997). Mice fed 1% CLA showed variable expression of Flk-1 protein, and animals fed 2% CLA showed uniformly low expression. Quantitation by scanning densitometry (FIG. 6B) demonstrated a statistically significant decrease in both the 200 kDa and 60 kDa Flk-1 antibody-reactive bands. This downregulation occurred in a dose-dependent manner (FIG. 6B).

Purified CLA Isomers Inhibit the Formation of Microcapillary Networks In Vitro

Figure 7:
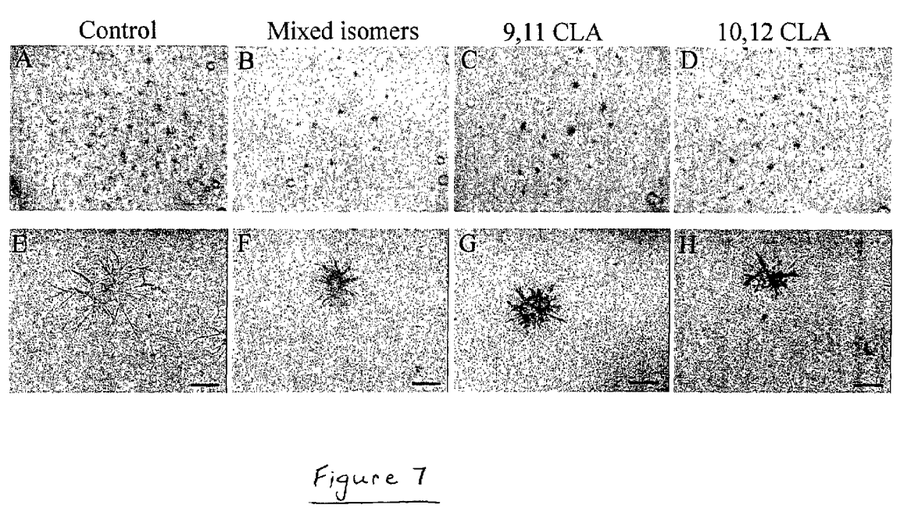
FIG. 7 is a low power photomicrograph showing the number and size of capillary networks for: control mammary stromal cells (MSC) (A,E), MSC cultured with mixed CLA isomers (B,F), MSC cultured with c9, t11 CLA (C,G) or t10, c12 CLA (D,H). These panels demonstrate the inhibition of in vitro vasculogenesis by CLA. A–D are scanned images of single wells on a 24-well tissue culture plate showing representative data that the number of capillary networks is decreased by all CLA isomers (well size is 1.4 cm in diameter, and the wells were scanned at 1× magnification; a central portion of each well is shown) E–H are higher power images showing that the size of the capillary network is decreased by all CLA isomers (the magnification bars in E–H are 200 $\mu$m).
Figure 8:
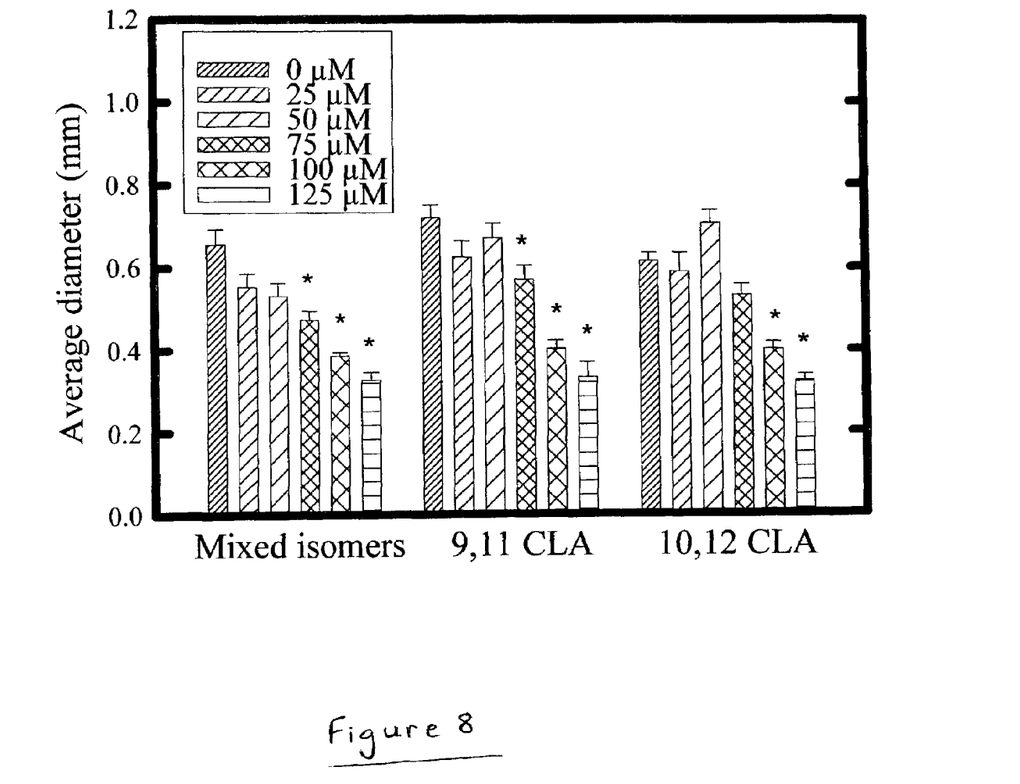
FIG. 8 is a plot of CLA isomers or CLA isomer blends versus average diameter of capillaries showing that CLA decreases diameter of mammary stromal cell capillary networks in vitro.

In order to determine which isomer of CLA may be critical in mediating its effects in vivo, and whether CLA is able to act directly on endothelial precursors, we used an in vitro angiogenesis assay to compare the ability of purified isomers of c9,t11- and t10,c12-CLA, as well as the mixed isomer preparation, to affect microcapillary plexus formation by mammary stromal vascular cells. Both the total number of colonies (FIGS. 7A–D) and the size/extent of their branching into the angiogenic substrate (FIGS. 7E–H) were inhibited by the presence of CLA. FIG. 8 shows the quantification of the effect of CLA on microcapillary network size. Both mixed isomers and c9,t11-CLA significantly decreased network diameter at the three highest concentration tested (75, 100 and 125 $\mu$M). In contrast, t10,c12-CLA significant decreased network size at the two highest concentrations tested (100 and 125 $\mu$M).

The data and teachings presented herein permit one skilled in the art to produce compositions of specific blends of CLA isomers to promote the desired effect of inhibiting the formation of new blood vessels in adults at risk for cancer, or in adults with cancer. Modification to the present invention that are within the purview of those skilled in the art are intended to be within the scope of this invention.

REFERENCES

1. Belury, Mass., Nickel, K P, Bird, C E, and Wu, Y M., (1996), Nutr. Cancer 26:149–157.
2. Cesano, A, Visonneau, S, Scimeca, J A, Kritchevsky, D, and Santoli, D., (1998), Anticancer Res., 18:1429–1434.
3. Chin, SF, Liu, W, Stockson, J M, Ha, Y L, and Pariza, M W., (1992), J. Food Comp. Anal., 5:185–197.
4. Darcy, K M, Zangani, D, Lee, P—P H, and Ip, M M., (2000), In: Methods in Mammary Gland Biology and Breast Cancer Research" eds. MM Ip and B B Asch. Kluwer Academic/Plenum Publishers, New York, 2000, pp 163–175.
5. Garcia, HS, Storkson, J M Pafiza M W, and Hill, C G, Jr., (1998), Biotechnol. Lett. 20:393–395.
6. Ha, Y L, Grimm, N K, and Pariza, M W., (1987), Carcinogenesis 8:1881–1887.
7. Ha, Y L, Storkson, J, and Pariza, M W., (1990), Cancer Res. 50:10971101.
8. 1p, C, Chin, S F, Scimeca, J A, and Pariza, M W., (1991), Cancer Res. 51:6118–6124.
9. Ip, C, Scimeca, J A, and Thompson, H., (1995), Nutr. Cancer 24:241–247.
10. Ip, C, Singh, M, Thompson, H J, and Scimeca, J A., (1994), Cancer Res. 54:1212–1215.
11. Kelly, M L, Berry, J R, Dwyer, D A, Griinari, J M, Chouinard, P Y, Van Amburgh, M E, and Bauman, Del., (1998), J. Nutr. 128:881–885.
12. Kibbey, M. C., Grant, D. S., and Kleinman, H. K., (1992), J. Nat. Canc. Inst., 84: 1633–1638.
13. Lavillonniere, F, Martin, J C, Bougnoux, P, and Sebedio, J L., (1998), J. Am. Oil Chem. Soc. 75:343–352.
14. Liew, C, Schut, H A J, Chin, S F, Pariza, M W, and Dashwood, R H., (1995), Carcinogenesis 16:3037–3043.
15. Parodi, P W. (1997)., J. Dairy Res. 60:1550–1553.
16. Sehat, N, Kramer, J K Mossoba, M M Yurawecz, M P, Roach, J A, Eulitz, K., Morehouse, K M, and Ku, Y., (1998), Lipids 33:963–971.
17. Stanton, C, Lawless, F, Kjellmer, G, Harrington, D, Devery, R, Connolly, J F, and Murphy, J., (1997), J. Food Sci. 62:1083–1086.
18. Takahashi, T. and Shibuya, M., (1997), Oncogene, 14: 2079–2089, 1997.
19. Visonneau, S, Cesano, A, Tepper, SA, Scimeca, J A, Santoli, D, and Kritchevsky, D., (1997), Anticancer Res. 17:969–973.
20. Yurawecz, M P, Roach, JAG, Sehat, N, Mossoba M M, Kramer, J K G, Fritsche, J, Steinhart, H and Ku, Y., (1998), Lipids 33:803–809.
21. Zangani, D, Darcy, K M, Masso-Welch, Pa., Bellamy, E S, Desole, M S, and Ip, MM., (1999), Differentiation 64:91–101.

What is claimed is:

1. A method for inhibition of angiogenesis in an individual diagnosed with a solid tumor consisting of the step of administering orally to the individual a therapeutically effective dose of one or more conjugated linoleic acid isomers, wherein angiogenesis in the tumor is inhibited following administration of the one or more conjugated linoleic acid isomers.

2. The method of claim 1, wherein the conjugated linoleic acid isomer is 7,9 conjugated linoleic acid.

3. The method of claim 1, wherein the conjugated linoleic acid isomer is 8,10 conjugated linoleic acid.

4. The method of claim 1, wherein the conjugated linoleic acid isomer is 9,11 conjugated linoleic acid.

5. The method of claim 1, we the conjugated linoleic acid isomer is 10,12 conjugated linoleic acid.

6. The method of claim 1, wherein the conjugated linoleic acid isomer is 11,13 conjugated linoleic acid.

7. The method of claim 1, wherein the conjugated linoleic acid isomer is 12,14 conjugated linoleic acid.

8. The method of claim 1, wherein the tumor is a breast tumor.

9. The method of claim 1, wherein angiogenesis is evaluated by a criteria he group consisting of number of blood vessels or capillaries in the tumor, serum VEGF levels and serum VEGF receptor levels.

* * * * *